(12) United States Patent
DiNucci

(10) Patent No.: US 11,090,182 B1
(45) Date of Patent: Aug. 17, 2021

(54) ADJUSTABLE ORTHOTIC FOOT DEVICE

(71) Applicant: Kent R. DiNucci, Omaha, NE (US)

(72) Inventor: Kent R. DiNucci, Omaha, NE (US)

(*) Notice: Subject to any disclaimer, the term of this patent is extended or adjusted under 35 U.S.C. 154(b) by 14 days.

(21) Appl. No.: 16/517,955

(22) Filed: Jul. 22, 2019

Related U.S. Application Data

(60) Provisional application No. 62/735,418, filed on Sep. 24, 2018.

(51) Int. Cl.
| | |
|---|---|
| A43B 7/14 | (2006.01) |
| A43B 9/12 | (2006.01) |
| A43B 17/00 | (2006.01) |
| A61F 5/14 | (2006.01) |
| A43B 7/24 | (2006.01) |
| A43B 13/12 | (2006.01) |

(52) U.S. Cl.
CPC .............. *A61F 5/14* (2013.01); *A43B 7/142* (2013.01); *A43B 7/1465* (2013.01); *A43B 9/125* (2013.01); *A43B 17/006* (2013.01); *A43B 7/141* (2013.01); *A43B 7/144* (2013.01); *A43B 7/24* (2013.01); *A43B 13/12* (2013.01)

(58) Field of Classification Search
CPC ..... A43B 3/0031; A43B 3/246; A43B 7/1465; A43B 7/148; A43B 9/125; A43B 17/006
See application file for complete search history.

(56) References Cited

U.S. PATENT DOCUMENTS

| | | | | |
|---|---|---|---|---|
| 1,690,964 A | * | 11/1928 | Balaskas ............... | A43B 7/142 36/164 |
| 1,729,725 A | * | 10/1929 | Krebs ................... | A43B 7/142 36/159 |
| 1,797,143 A | * | 3/1931 | Havey ................... | A43B 7/144 36/164 |
| 1,957,695 A | * | 5/1934 | Chiappetta ............ | A43B 7/22 36/181 |
| 2,247,114 A | * | 6/1941 | Boos ..................... | A43B 7/142 36/147 |
| 3,084,695 A | | 4/1963 | O'Donnell | |
| 3,339,555 A | * | 9/1967 | Rotko .................. | A43B 7/1465 36/165 |
| 4,813,157 A | * | 3/1989 | Boisvert ............... | A43B 7/142 36/145 |
| 4,918,776 A | * | 4/1990 | Motoda ................. | A43B 9/12 12/142 F |
| 4,969,224 A | * | 11/1990 | Birke .................... | A43B 9/00 12/142 F |
| 5,069,212 A | | 12/1991 | Cohen | |

(Continued)

*Primary Examiner* — Sharon M Prange
(74) *Attorney, Agent, or Firm* — Suiter Swantz pc llo

(57) ABSTRACT

In embodiments, an adjustable orthotic foot device may include a shell layer including an upper surface and a contoured lower surface, and a soft insole layer coupled to the upper surface of the shell layer, the soft insole layer defining an arch support structure on an upper surface of the soft insole layer along a medial edge of the soft insole layer. The adjustable orthotic foot device may further include one or more structural support inserts configured to be removably inserted within a pocket formed between the shell layer and the soft insole layer in order to adjust an arch height of the arch support structure. In embodiments, the one or more structural support inserts may be defined by a curved lateral edge and a convex curved medial edge.

18 Claims, 18 Drawing Sheets

(56) References Cited

U.S. PATENT DOCUMENTS

| | | | | |
|---|---|---|---|---|
| 5,138,774 A | * | 8/1992 | Sarkozi | A43B 7/14 |
| | | | | 36/159 |
| 5,388,351 A | | 2/1995 | Mitchell et al. | |
| 5,400,528 A | | 3/1995 | Skinner et al. | |
| 6,000,147 A | * | 12/1999 | Kellerman | A43B 7/142 |
| | | | | 36/160 |
| 6,823,550 B2 | | 11/2004 | Kantro | |
| 6,920,707 B1 | | 7/2005 | Greene et al. | |
| 7,373,740 B2 | | 5/2008 | Lo | |
| 7,681,333 B2 | * | 3/2010 | Dardinski | A43B 7/1425 |
| | | | | 36/100 |
| 8,463,657 B1 | * | 6/2013 | Bentvelzen | A43B 19/00 |
| | | | | 705/26.1 |
| 8,667,716 B2 | * | 3/2014 | Torrance | A43B 7/1465 |
| | | | | 36/159 |
| 2007/0289170 A1 | | 12/2007 | Avent et al. | |
| 2008/0005931 A1 | | 1/2008 | Ellis, III | |
| 2008/0047164 A1 | * | 2/2008 | Vindriis | A43B 7/1425 |
| | | | | 36/29 |
| 2008/0178493 A1 | * | 7/2008 | Scofield | A43B 7/1465 |
| | | | | 36/43 |
| 2009/0049712 A1 | | 2/2009 | Steszyn et al. | |
| 2011/0072685 A1 | * | 3/2011 | Gutowsky, Jr. | A43B 7/1445 |
| | | | | 36/44 |
| 2014/0259752 A1 | * | 9/2014 | Feldman | A43B 7/1465 |
| | | | | 36/43 |
| 2015/0230551 A1 | * | 8/2015 | O'Brien | A43B 17/105 |
| | | | | 36/44 |
| 2016/0150854 A1 | * | 6/2016 | Hockerson | A43B 3/0005 |
| | | | | 36/28 |

* cited by examiner

400

402 — FORMING A SHELL LAYER INCLUDING AN UPPER SURFACE AND A CONTOURED LOWER SURFACE, WHEREIN THE CONTOURED LOWER SURFACE OF THE SHELL LAYER IS CONTOURED SUCH THAT IT CONFORMS TO AT LEAST A PORTION OF A PROFILE OF A FOOTWEAR ARTICLE WHEN DISPOSED WITHIN THE FOOTWEAR ARTICLE

404 — FORMING A SOFT INSOLE LAYER DEFINING AN ARCH SUPPORT STRUCTURE ON AN UPPER SURFACE OF THE SOFT INSOLE LAYER ALONG A MEDIAL EDGE OF THE SOFT INSOLE LAYER

406 — COUPLING A REMOVABLE PLASTIC LAYER TO A FIRST PORTION OF A LOWER SURFACE OF THE SOFT INSOLE LAYER, WHEREIN THE FIRST PORTION OF THE LOWER SURFACE OF THE SOFT INSOLE LAYER IS DIRECTLY BENEATH THE ARCH SUPPORT STRUCTURE OF THE SOFT INSOLE LAYER

408 — COUPLING THE REMOVABLE PLASTIC LAYER AND A SECOND PORTION OF THE SOFT INSOLE LAYER DIFFERENT FROM THE FIRST PORTION TO THE UPPER SURFACE OF THE SHELL LAYER

FIG.4

ADJUSTABLE ORTHOTIC FOOT DEVICE

CROSS-REFERENCE TO RELATED APPLICATION

The present application claims the benefit under 35 U.S.C. § 119(e) of U.S. Provisional Application Ser. No. 62/735,418, filed Sep. 24, 2018, entitled ADJUSTABLE ORTHOTIC FOOT DEVICE, naming Kent R. DiNucci as inventor, which is incorporated herein by reference in the entirety.

TECHNICAL FIELD

The present disclosure generally relates to the field of footwear, and more particularly to an adjustable orthotic foot device.

BACKGROUND

Orthotic devices are commonly employed as removable insoles into footwear to improve comfort and stability for a user. Conventional orthotic devices may be classified as general orthotic devices or customized orthotic devices which are constructed for a particular user. Due to the fact that everyone has a unique foot structure, a general orthotic device is rarely substantially helpful. Conversely, while customized orthotic devices may be configured for particular users, the cost of customized orthotic devices is often prohibitively high, preventing many users from gaining access to orthotic devices they require.

Therefore, there exists a need for a system and method which cure one or more of the shortfalls of previous approaches identified above.

SUMMARY

An adjustable orthotic foot device is disclosed. The adjustable orthotic foot device may include a shell layer including an upper surface and a contoured lower surface, wherein the contoured lower surface of the shell layer is contoured such that it conforms to at least a portion of a profile of an inner surface of a footwear article when disposed within the footwear article. The adjustable orthotic foot device may further include a soft insole layer coupled to the upper surface of the shell layer, the soft insole layer defining an arch support structure on an upper surface of the soft insole layer along a medial edge of the soft insole layer, wherein the soft insole layer is formed with one or more elastically compressible materials. The adjustable orthotic foot device may further include one or more structural support inserts configured to be removably inserted within a pocket formed between the shell layer and the soft insole layer directly beneath the arch support structure in order to adjust an arch height of the arch support structure. In embodiments, the one or more structural support inserts may be defined by a curved lateral edge and a curved medial edge, wherein the curved medial edge comprises a convex curve with respect to a central plane of the adjustable orthotic foot device. In embodiments, the one or more structural support inserts may be configured to be removably inserted within the pocket such that the medial edge of the one or more structural support inserts are substantially flush with the medial edge of the soft insole layer.

An adjustable orthotic foot device is disclosed. In embodiments, the adjustable orthotic foot device may include a shell layer and a soft insole layer coupled to an upper surface of the shell layer, the soft insole layer defining an arch support structure on an upper surface of the soft insole layer along a medial edge of the soft insole layer. The adjustable orthotic foot device may further include a removable plastic layer disposed between a portion of the upper surface of the shell layer and a portion of a lower surface of the soft insole layer, wherein removal of the removable plastic layer from between the shell layer and the soft insole layer forms a pocket between the shell layer and the soft insole layer below the arch support structure. The adjustable orthotic foot device may further include one or more structural support inserts configured to be removably inserted within the pocket formed between the shell layer and the soft insole layer to adjust an arch height of the arch support structure, wherein the one or more structural support inserts are configured to be removably inserted within the pocket such that the medial edge of the one or more structural support inserts are substantially flush with the medial edge of the soft insole layer.

A method of producing an adjustable orthotic foot device is disclosed. The method may include: forming a shell layer including an upper surface and a contoured lower surface, wherein the contoured lower surface of the shell layer is contoured such that it conforms to at least a portion of a profile of a footwear article when disposed within the footwear article; forming a soft insole layer defining an arch support structure on an upper surface of the soft insole layer along a medial edge of the soft insole layer; coupling a removable plastic layer to a first portion of a lower surface of the soft insole layer, wherein the first portion of the lower surface of the soft insole layer is directly beneath the arch support structure of the soft insole layer; and coupling the removable plastic layer and a second portion of the soft insole layer different from the first portion to the upper surface of the shell layer.

It is to be understood that both the foregoing general description and the following detailed description are exemplary and explanatory only and are not necessarily restrictive of the present disclosure. The accompanying drawings, which are incorporated in and constitute a part of the specification, illustrate the subject matter of the disclosure. Together, the descriptions and the drawings serve to explain the principles of the disclosure.

BRIEF DESCRIPTION OF THE DRAWINGS

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings:

FIG. 1I is a side view of an adjustable orthotic foot device including two structural support inserts, in accordance with one or more embodiments of the present disclosure.

FIG. 4 is a flowchart of a method for producing an adjustable orthotic foot device, in accordance with one or more embodiments of the present disclosure.

DETAILED DESCRIPTION

Figure 1A:
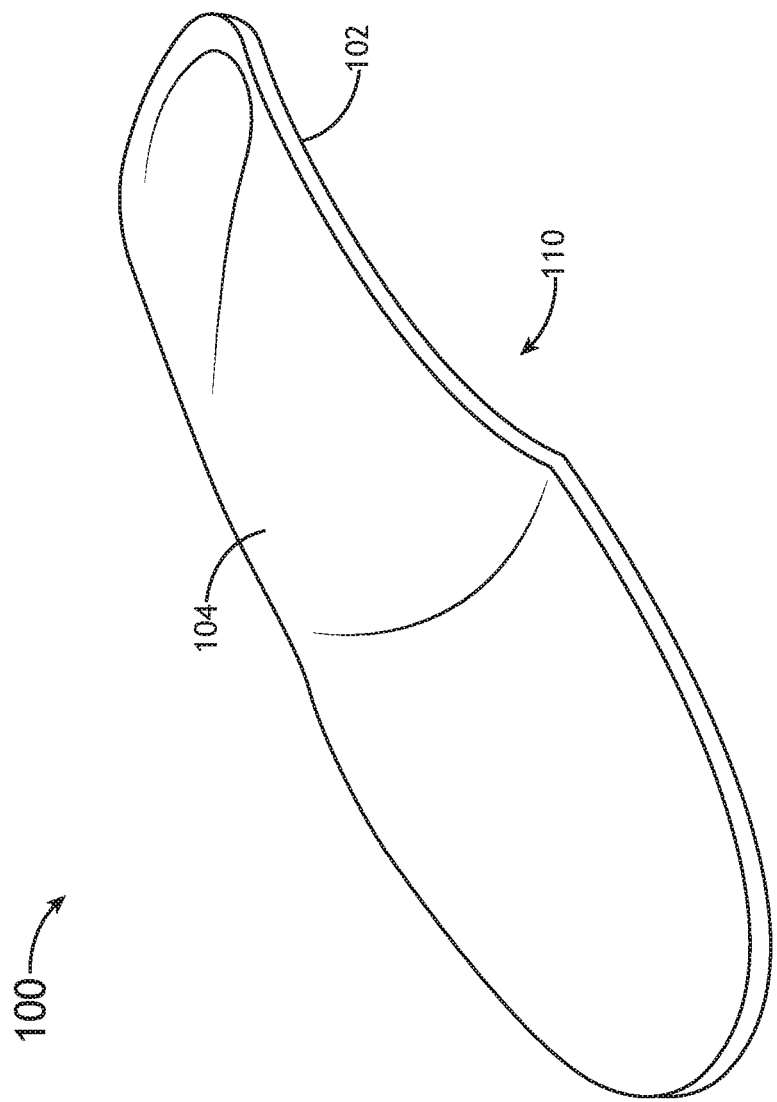
FIG. 1A is a perspective view of an adjustable orthotic foot device, in accordance with one or more embodiments of the present disclosure.

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of sub-combination of two or more such features, along with any other features which may not necessarily be expressly described or inherently present in the instant disclosure.

As noted previously herein, orthotic devices are commonly employed as removable insoles into footwear to improve comfort and stability for a user. Conventional orthotic devices may be classified as general orthotic devices or customized orthotic devices which are constructed for a particular user. Due to the fact that everyone has a unique foot structure, a general orthotic device is rarely substantially helpful. Conversely, while customized orthotic devices may be configured for particular users, the cost of customized orthotic devices is often prohibitively high, preventing many users from gaining access to orthotic devices they require.

Accordingly, embodiments of the present disclosure are directed to a system and method which cure one or more of the shortfalls of previous approaches identified above. Embodiments of the present disclosure are directed to an adjustable orthotic foot device. Additional embodiments of the present disclosure are directed to an adjustable orthotic foot device which includes a shell layer and a soft insole layer disposed on top of the shell layer. Further embodiments of the present disclosure are directed to an adjustable orthotic device configured to receive one or more structural support inserts within a pocket between the shell layer and the soft insole layer in order to adjust the size of an arch of the adjustable orthotic foot device. It is contemplated that one or more structural support inserts may be insertable within the pocket between the shell layer and the soft layer in order to provide a desired amount of arch support for a particular user.

Figure 1B:
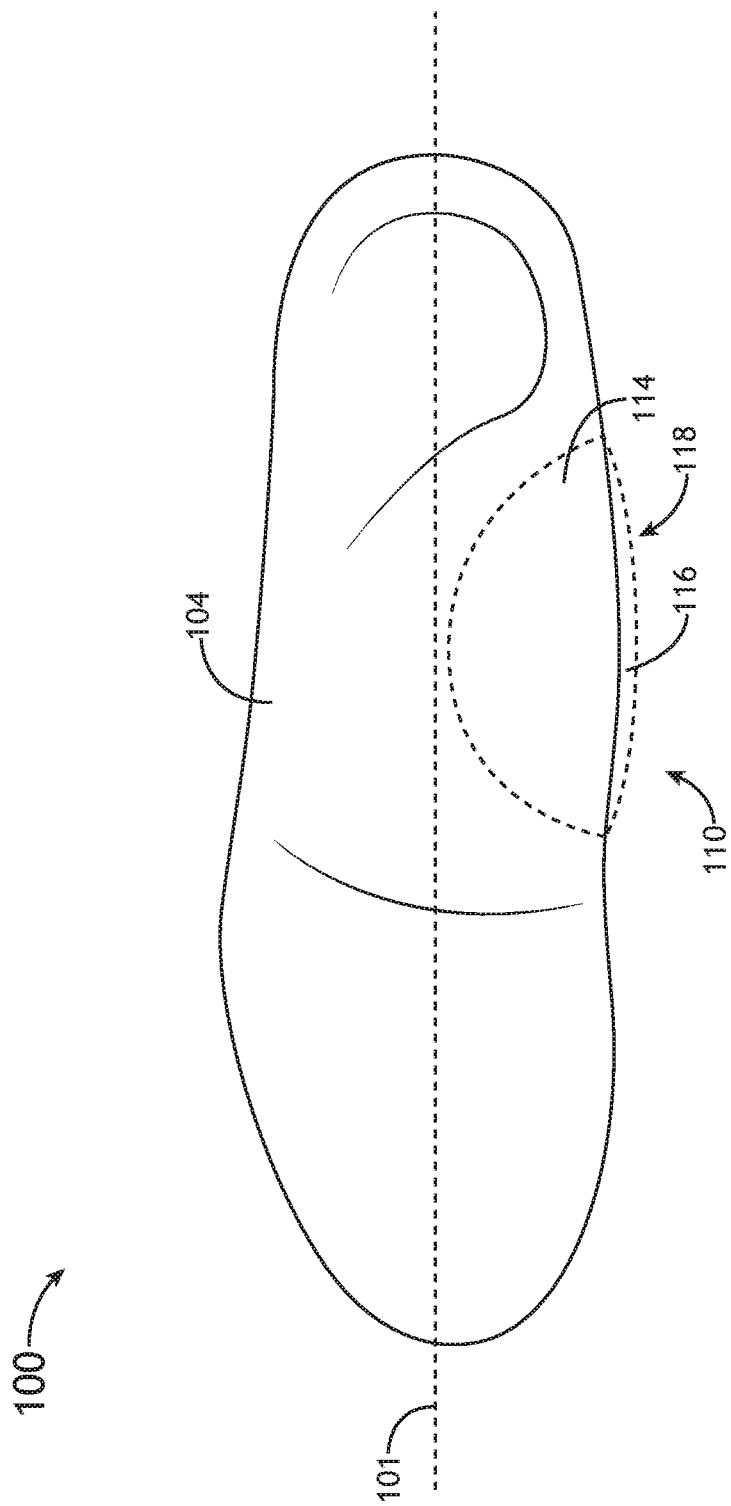
FIG. 1B is a top view of an adjustable orthotic foot device, in accordance with one or more embodiments of the present disclosure.
Figure 1C:
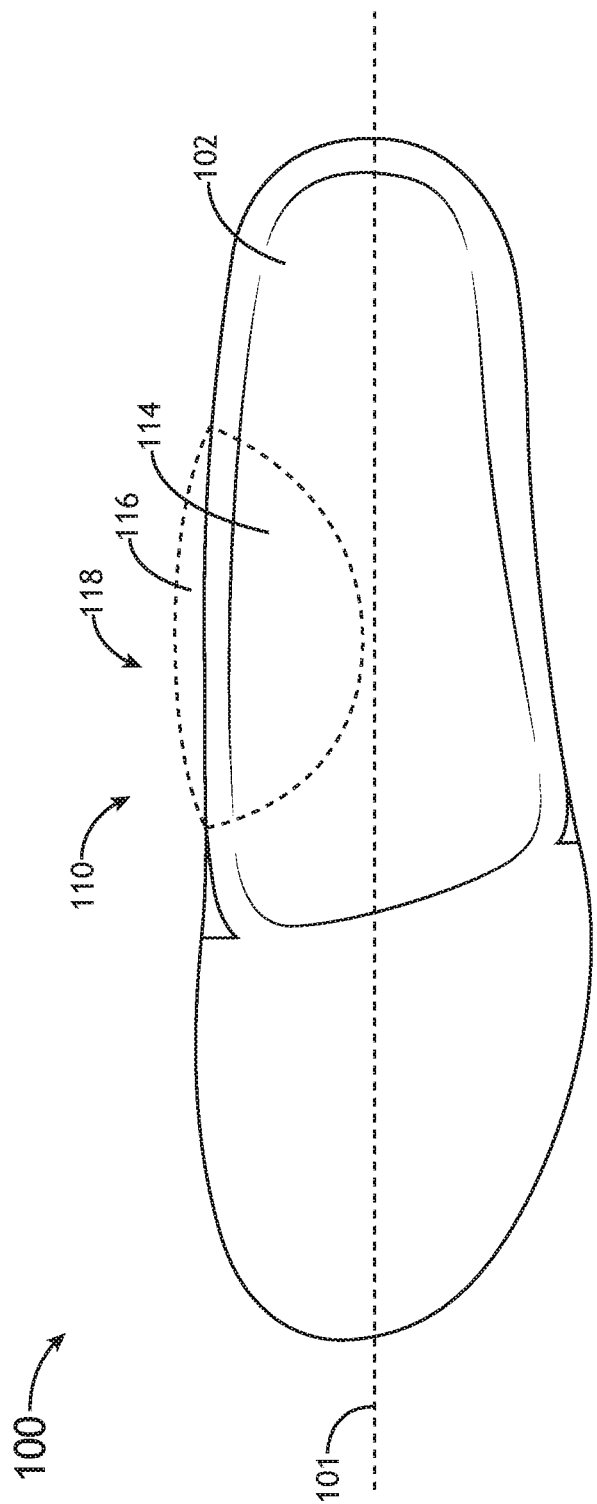
FIG. 1C is a bottom view of an adjustable orthotic foot device, in accordance with one or more embodiments of the present disclosure.
Figure 1D:
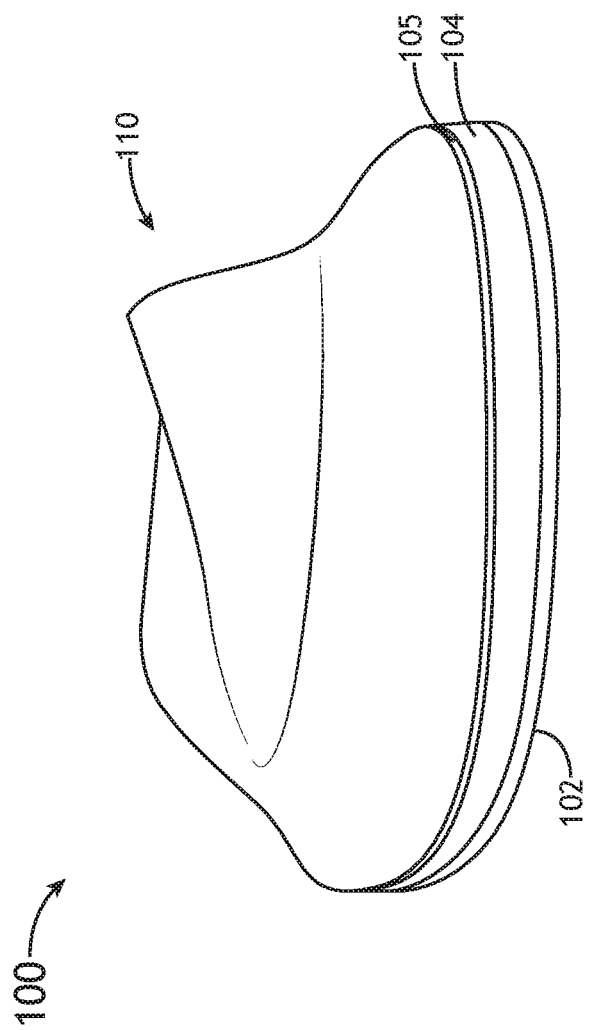
FIG. 1D is a front elevation view of an adjustable orthotic foot device, in accordance with one or more embodiments of the present disclosure.
Figure 1E:
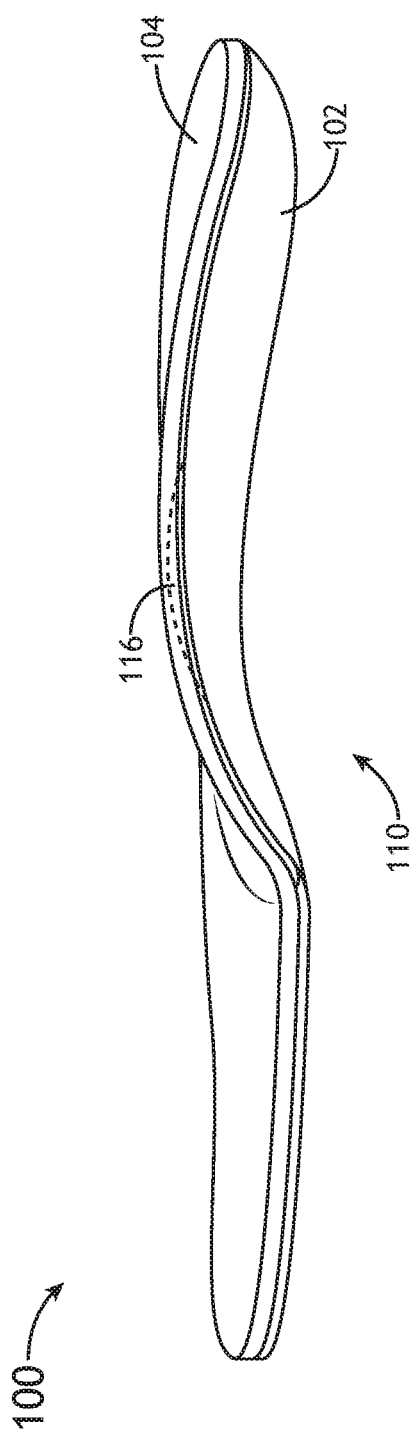
FIG. 1E is a side elevation view of an adjustable orthotic foot device, in accordance with one or more embodiments of the present disclosure.

FIG. 1A is a perspective view of an adjustable orthotic foot device 100, in accordance with one or more embodiments of the present disclosure. FIG. 1B is a top view of an adjustable orthotic foot device 100, in accordance with one or more embodiments of the present disclosure. FIG. 1C is a bottom view of an adjustable orthotic foot device 100, in accordance with one or more embodiments of the present disclosure. FIG. 1D is a front elevation view of an adjustable orthotic foot device 100, in accordance with one or more embodiments of the present disclosure. FIG. 1E is a side elevation view of an adjustable orthotic foot device 100, in accordance with one or more embodiments of the present disclosure.

The adjustable orthotic foot device 100 may include, but is not limited to, a shell layer 102 and a soft insole layer 104. In embodiments, the adjustable orthotic foot device 100 may also include, but is not limited to, one or more structural support inserts 108 and a removable plastic layer 116.

In embodiments, the adjustable orthotic foot device 100 is configured to be inserted within a footwear article of a user in order to provide enhanced support and comfort for the user. The adjustable orthotic foot device 100 of the present disclosure may be implemented in the context of any footwear article known in the art including, but not limited to, tennis shoes, running shoes, dress shoes, boots, sandals, heeled shoes, and the like.

The shell layer 102 may be configured as a bottom layer of the adjustable orthotic foot device 100 such that a bottom surface of the shell layer 102 makes up at least a portion of a bottom surface of the adjustable orthotic foot device 100. For example, the shell layer 102 may cover the entire bottom surface of the adjustable orthotic foot device 100. By way of another example, as shown in FIG. 1C, the shell layer 102 may be coupled to the soft insole layer 104 only under a user's heel and midfoot. In this example, a bottom surface of the shell layer 102 may make up only a portion of a bottom surface of the adjustable orthotic foot device 100 as a whole. In embodiments, the shell layer 102 of the adjustable orthotic foot device 100 may include a contoured lower surface, wherein the contoured lower surface of the shell layer 102 is contoured such that it conforms to at least a portion of a profile of an inner surface of a footwear article.

In embodiments, the shell layer 102 may be contoured such that it conforms to the general shape of a user's foot. For example, it is contemplated that the shell layer 102 may include a heat-moldable shell which may be moldable to a user's foot. In some embodiments, the shell layer 102 may define an arch support structure 110 along a medial edge of the shell layer 102. The arch support structure 110 may be configured to provide support to the arch of a user's foot. In embodiments, arch support structure 110 of the shell layer 102 may include a built-in metatarsal bar. In additional and/or alternative embodiments, the arch support structure 110 of the shell layer may include a built-in first ray cut-out to allow more motion of the first ray of the foot. It is noted herein that such first ray cut-outs are typically only in expensive, custom orthotic devices.

The shell layer 102 may be configured to provide structural support to a user's foot within a footwear article. In this regard, the shell layer 102 may be stiff enough to hold up the arch of a user's foot, but not too stiff to resist the natural position of the foot of the user when using the adjustable orthotic foot device 100. In some embodiments, the shell layer 102 may operate as a shock absorber to decrease strain and stress of the structures of the foot and ankle. The shell layer 102 may be formed of any material known in the art including, but not limited to, plastic, ethylene vinyl acetate, and the like.

In embodiments, the adjustable orthotic foot device 100 includes a soft insole layer 104 coupled to the upper surface of the shell layer 102. The soft insole layer 104 may be coupled to the shell layer 102 using any techniques known in the art including, but not limited to, one or more adhesives. In embodiments, the soft insole layer 104 is configured to provide further comfort and support to the foot of a user. The soft insole layer 104 may be formed using any materials known in the art. For example, the soft insole layer 104 may include, but is not limited to, a cushion material, a foam material, polyurethane, and the like. By way of another example, the soft insole layer 104 may include an anti-bacterial material, a fungicidal material, and/or an anti-odorous material. For instance, the soft insole layer 104 may include a bamboo or charcoal fiber material.

In embodiments, the soft insole layer 104 may be formed from a material which is configured to be compressed under the weight of a user, but which rebounds to its original form/structure when not exposed to the user's weight. For example, the soft insole layer 104 may be formed with one or more materials which are able to rebound with each step of a user, no matter the pace of the user's gait, in order to provide the user with consistent comfort and support throughout their stride. Accordingly, the soft insole layer 104 may be formed from one or more elastically compressible materials.

The soft insole layer 104 may be coupled/disposed on the shell layer 102 such that the upper surface of the soft insole layer 104 substantially conforms to the contours of an upper surface of the shell layer 102. In this regard, the upper surface of the soft insole layer 104 may define the upper surface of the arch support structure 110 which comes into contact with a user's foot.

The adjustable orthotic foot device 100 may include any number of additional layers known in the art. For example, as shown in FIG. 1D, the adjustable orthotic foot device 100 may include one or more fabric layers 105 disposed on a top surface of the soft insole layer 104. It is contemplated herein that the fabric layer 105 may include a fabric which is configured to provide support and comfort to the foot of a user, while also preventing moisture and/or odor from permeating the adjustable orthotic foot device 100.

In embodiments, the soft insole layer 104 may define an arch support structure 110 on an upper surface of the soft insole layer 104 along a medial edge of the soft insole layer 104. For example, as shown in FIG. 1A and FIG. 1D, the soft insole layer 104 may define an arch support structure 110 which substantially corresponds to the shape and form of the arch support structure 110 defined by the shell layer 102. In this regard, the arch support structure 110 may be said to be defined by the collective shape of the shell layer 102 and the soft insole layer 104. As shown in FIG. 1B, the medial edge of the soft insole layer 104 along which the arch support structure 110 is disposed may be curved. For example, the curved medial edge of the soft insole layer 104 may include a convex medial edge with respect to the central plane 101 of the adjustable orthotic foot device 100.

It is contemplated herein that a profile of an upper surface of the adjustable orthotic foot device 100 may be adjusted by inserting one or more removable structural support inserts 108 within one or more pockets 114 of the adjustable orthotic foot device 100. In this regard, the adjustable foot orthotic device 100 may include one or more pockets 114 configured to receive one or more structural support inserts 108. This may be further understood with reference to FIGS. 1F-1G.

Figure 1F:
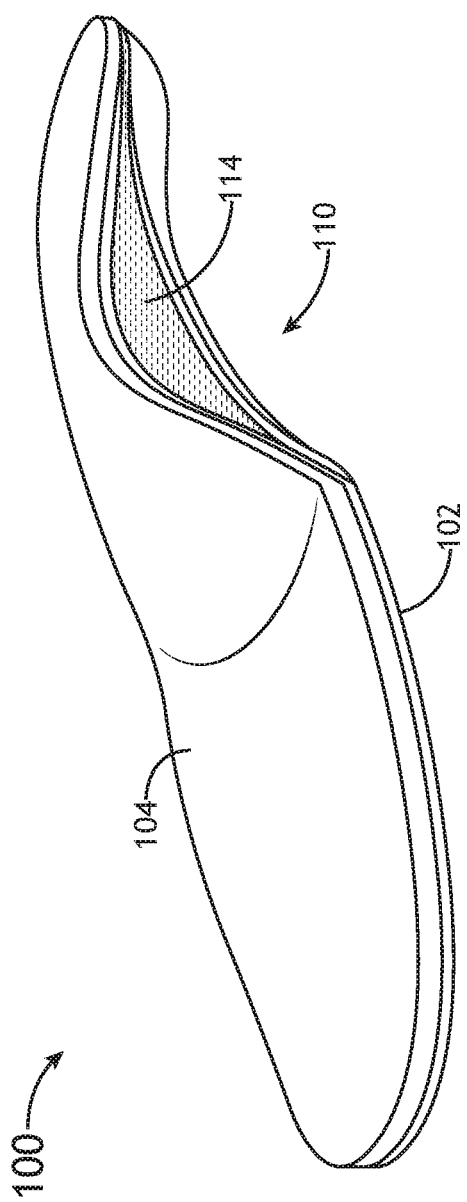
FIG. 1F is a perspective view of a pocket of an adjustable orthotic foot device, in accordance with one or more embodiments of the present disclosure.
Figure 1G:
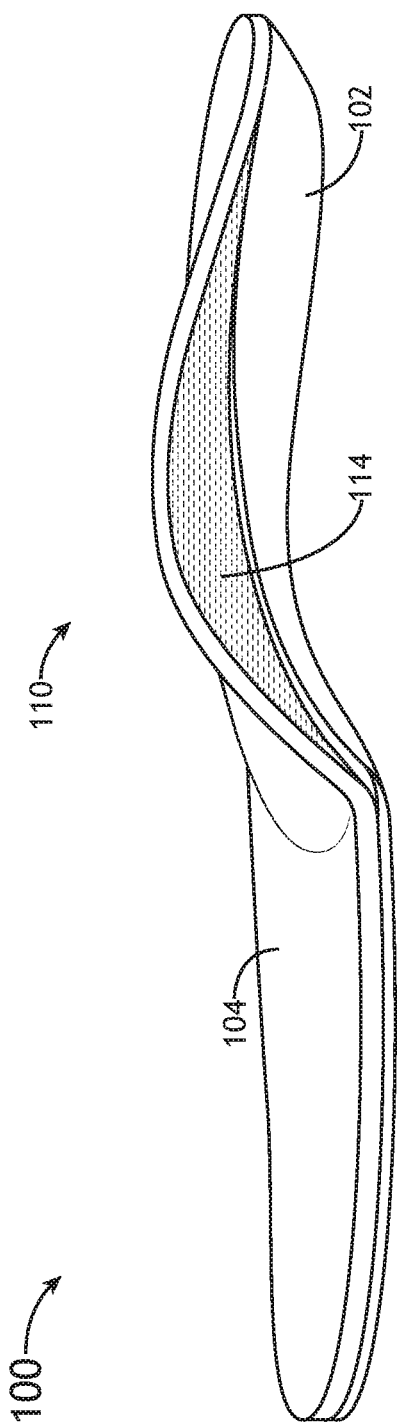
FIG. 1G is a side elevation view of a pocket of an adjustable orthotic foot device, in accordance with one or more embodiments of the present disclosure.

FIG. 1F is a perspective view of a pocket 114 of an adjustable orthotic foot device 100, in accordance with one or more embodiments of the present disclosure. FIG. 1G is a side elevation view of a pocket 114 of an adjustable orthotic foot device 100, in accordance with one or more embodiments of the present disclosure.

The adjustable foot orthotic device 100 may include one or more pockets 114 formed between the shell layer 102 and the soft insole layer 104. For example, as shown in FIGS.

1F-1G, the adjustable orthotic foot device 100 may include a pocket 114 disposed between the shell layer 102 and the soft insole layer 104 directly beneath the top profile of the arch support structure 110. In this regard, the pocket 114 may be defined by a portion of a lower surface of the soft insole layer 104, and a portion of an upper surface of the shell layer 102. In embodiments, the adjustable orthotic foot device 100 may include one or more structural support inserts 108 configured to be removably inserted within one or more pockets 114 of the adjustable orthotic foot device 100 (e.g., pocket 114). It is contemplated herein that the one or more structural support inserts 108 may be removably inserted within the pocket 114 in order to adjust a profile and/or height of the arch support structure 110. This may be further understood with reference to FIGS. 1H-1J.

Figure 1H:
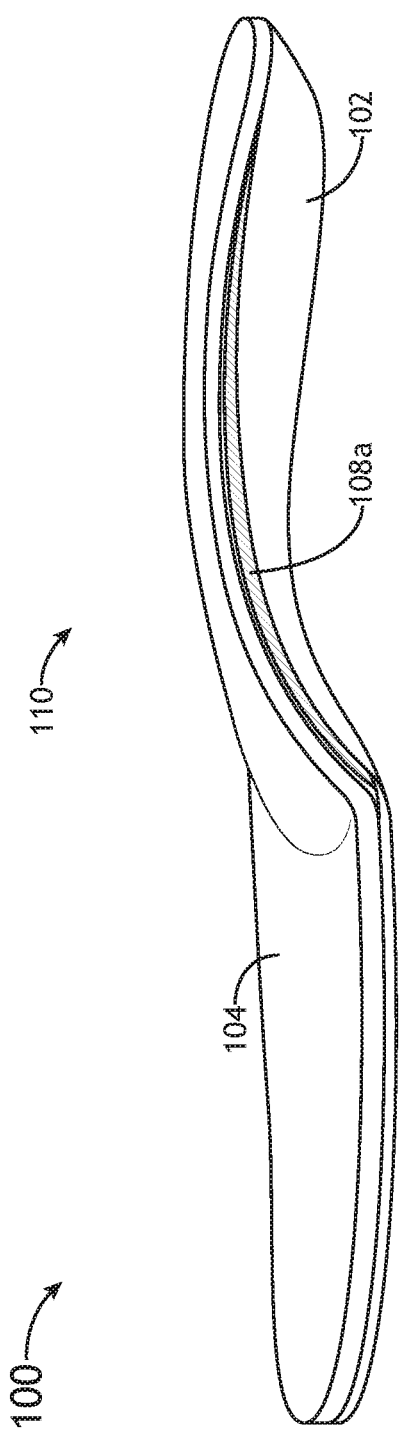
FIG. 1H is a side view of an adjustable orthotic foot device including one structural support insert, in accordance with one or more embodiments of the present disclosure.
Figure 11:
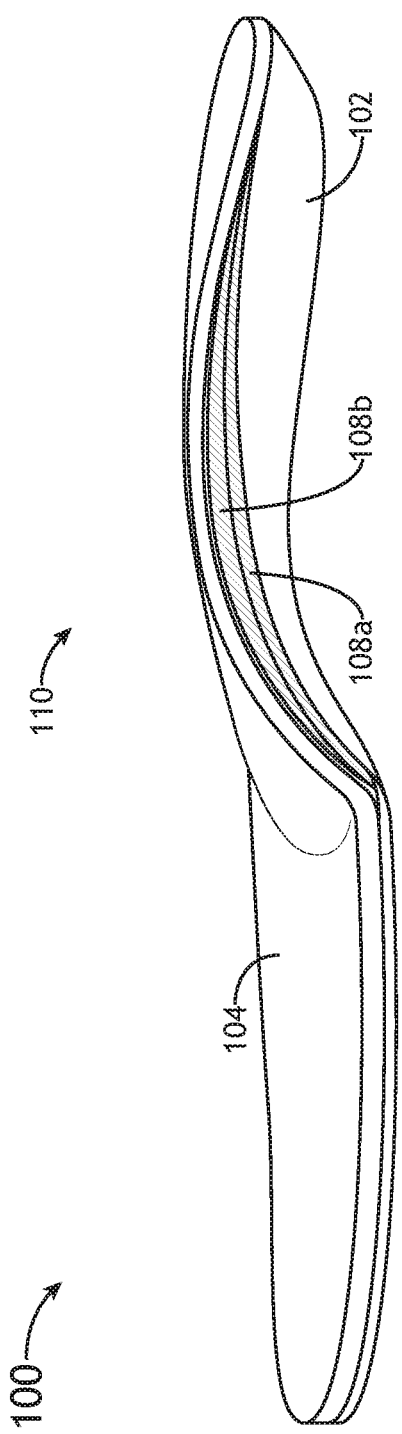
Figure 1J:
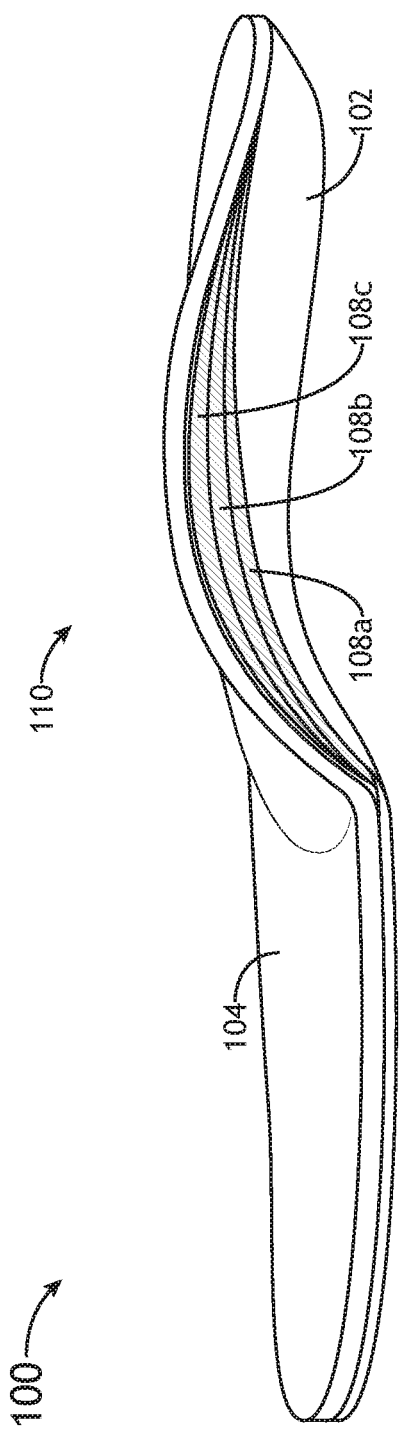
FIG. 1J is a side view of an adjustable orthotic foot device including three structural support inserts, in accordance with one or more embodiments of the present disclosure.

FIG. 1H is a side view of an adjustable orthotic foot device 100 including one structural support insert 108, in accordance with one or more embodiments of the present disclosure. FIG. 1I is a side view of an adjustable orthotic foot device 100 including two structural support inserts 108, in accordance with one or more embodiments of the present disclosure. FIG. 1J is a side view of an adjustable orthotic foot device including three structural support inserts, in accordance with one or more embodiments of the present disclosure.

As shown in FIGS. 1H-1J, one or more structural support inserts 108a, 108, 108c may be removably inserted within the pocket 114 in order to adjust a height and/or profile of the arch support structure 110. For example, as shown in FIG. 1I, a first structural support insert 108a may be configured to be removably inserted within the pocket 114 such that it is disposed on the upper surface of the shell layer 102, and a second structural support insert 108b insert may be configured to be removably inserted within the pocket 114 between an upper surface of the first structural support insert 108a and a lower surface of the soft insole layer 104.

In some embodiments, the one or more structural support inserts 108 are configured to be removably inserted within the pocket 114 such that the medial edge(s) of the one or more structural support inserts are substantially flush with the medial edge of the shell layer 102 and/or soft insole layer 104. It is contemplated herein that disposing the one or more structural support inserts 108 within the pocket 114 such that they are flush with the medial edge of the adjustable orthotic foot device 100 may ensure a proper and secure fit of the adjustable orthotic foot device 100 within a footwear article.

In embodiments, the pocket 114 may include one or more adhesives configured to secure the one or more structural support inserts 108 within the pocket 114. For example, the portion of the lower surface of the soft insole layer 104 defining the upper surface of the pocket 114 may include one or more adhesives configured to secure the one or more structural support inserts 108 within the pocket 114. By way of another example, the portion of the upper surface of the shell layer 102 defining the lower surface of the pocket 114 may include one or more adhesives configured to secure the one or more structural support inserts 108 within the pocket 114.

While FIGS. 1H-1J illustrate up to three structural support inserts 108 disposed within the pocket 114, this is not to be regarded as a limitation of the present disclosure, unless noted otherwise herein. In this regard, it is contemplated that the adjustable orthotic foot device 100 may be configured to receive any number of structural support inserts 108 in order to provide the proper level of comfort and support to individual users on a bespoke basis. Furthermore, the use of the structural support inserts 108 of the present disclosure may allow for the adjustment of a profile of the adjustable orthotic foot device 100 along both the lateral arch and the medial arch, which is typically not possible with other conventional orthotic devices.

In some embodiments, the adjustable orthotic foot device 100 may further include a plastic layer 116 disposed between the shell layer 102 and the soft insole layer 104, as shown in FIG. 1E. The plastic layer 116 may exhibit a smaller cross-sectional area than the shell layer 102 and/or the soft insole layer 104, such that the plastic layer 116 is disposed between only a portion of the upper surface of the shell layer 102 and a portion of the lower surface of the soft insole layer 104. For example, the plastic layer 116 may be sized such that a cross sectional area of the plastic layer 116 defines a cross sectional area of the pocket 114. For instance, as shown in FIG. 1B, the cross-sectional area of the portion of the plastic layer 116 disposed between the shell layer 102 and the soft insole layer 104 may define the cross-sectional area of the pocket 114. In this regard, in some embodiments, the shape and size of the plastic layer 116 may define the shape and size of the pocket 114.

In embodiments, the plastic layer 116 may be removable. In embodiments where the plastic layer 116 includes a removable plastic layer 116, removal of the plastic layer 116 from between the shell layer 102 and the soft insole layer 104 may form the pocket 114. For example, the upper surface of the shell layer 102 may be coupled to the lower surface of the plastic layer 116 via one or more adhesives. Similarly, the lower surface of the soft insole layer 104 may be coupled to the upper surface of the plastic layer 116 via one or more adhesives. Upon removal of the plastic layer 116, the plastic layer 116 may separate from the shell layer 102 and the soft insole layer 104, thereby forming the pocket 114.

As shown in FIGS. 1B and 1C, the plastic layer 116 may include a pull tab portion 118 which extends beyond the medial edge of the soft insole layer 104 and/or medial edge of the shell layer 102. It is contemplated herein that the pull tab portion 118 may facilitate with removal of the plastic layer 116 by a user. In an additional and/or alternative embodiment where the plastic layer 116 is not removable, it is contemplated herein that the pull tab portion 118 of the plastic layer 116 may assist a user in opening the pocket 114 to facilitate addition and/or removal of one or more structural support inserts 108 from the pocket 114. For example, in some embodiments, the plastic layer 116 may be permanently coupled to the plastic layer 104 such that the pull tab portion 118 may assist a user in pulling the soft insole layer 104 away from the shell layer 102 in order to form the pocket 114.

In embodiments, the adjustable orthotic foot device 100 may be configured to function with or without any structural support inserts 108. In this regard, the adjustable orthotic foot device 100 may be configured to substantially close/collapse the pocket 114 when no structural support inserts 108 are disposed within the pocket 114. For example, referring to embodiments with a removable plastic layer 116, the adjustable orthotic foot device 100 may initially start with a closed/collapsed pocket 114, wherein the upper surface of the shell layer 102 and the lower surface of the soft insole layer 104 is coupled to the plastic layer 116 via one or more adhesives on the upper surface of the shell layer 102 and/or the lower surface of the soft insole layer 104. Upon removal of the plastic layer 116, a user may expose and open the pocket 114 in order to insert one or more structural support inserts 108. Subsequently, the user may decide to remove the one or more structural support inserts 108. Upon removal of the one or more structural support inserts 108, the void of the pocket 114 may be substantially closed and/or collapsed such that the lower surface of the soft insole layer 104 becomes coupled to the upper surface of the shell layer 102 via the one or more adhesives on the respective surfaces of the shell layer 102 and/or soft insole layer 104. In this regard, in the absence of any structural support inserts 108, the adjustable orthotic foot device 100 may be configured to close/collapse the one or more pockets 114 such that the adjustable orthotic foot device 100 may provide comfort and support via the shell layer 102 and soft insole layer 104 alone.

It is contemplated herein that additional and/or alternative embodiments may be utilized to form the pocket 114 and allow the adjustable orthotic foot device 100 to function without any structural support inserts 108. In particular, additional and/or alternative embodiments may be employed for creating and/or closing/collapsing the pocket 114. For example, referring to FIG. 1B, differences in processes and/or substances used to couple the shell layer 102 to the soft insole layer 104 may be used to form the pocket 114. For instance, a first set of one or more adhesives may be used to permanently couple the soft insole layer 104 to the shell layer 102 around the heel region, lateral midfoot region, and sole region of the adjustable orthotic foot device 100. Conversely, a second set of one or more adhesives may be configured to temporarily and/or impermanently couple the soft insole layer 104 to the shell layer 102 throughout a region defining the pocket 114. In this regard, a user may be able to separate the soft insole layer 104 from the shell layer 102 at the location of the pocket 114 to form the pocket 114, while the remainder of the soft insole layer 104 may remain coupled to the shell layer 102.

Figure 2A:
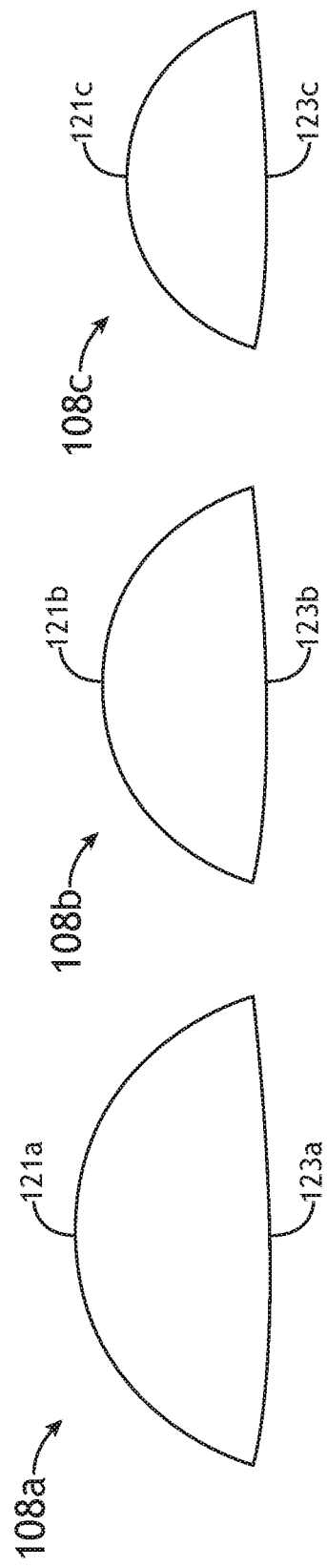
FIG. 2A is a top view of structural support inserts, in accordance with one or more embodiments of the present disclosure.

FIG. 2A is a top view of structural support inserts 108, in accordance with one or more embodiments of the present disclosure.

The structural support inserts 108 may be formed with any material known in the art. For example, the one or more structural support inserts 108 may be formed with one or more elastically compressible materials. In embodiments, the structural support inserts 108 may include one or more adhesives configured to secure the structural support inserts 108 within the pocket 114. For example, the upper surfaces and/or the lower surfaces of the one or more structural support inserts 108 may include one or more adhesives. In embodiments where the structural support inserts 108 include adhesives, the structural support inserts 108 may further include one or more removable covers disposed over the adhesives in order to preserve the adhesives until use. For example, where a structural support insert 108 includes adhesives on the upper surface and the lower surface, the structural support insert 108 may further include a first peel-off cover disposed over the adhesive on the upper surface, and a second peel-off cover disposed over the adhesive on the lower surface.

In embodiments, as shown in FIG. 2A, the one or more structural support inserts 108 may be defined by a lateral edge 121 and a medial edge 123. In some embodiments, at least one of the lateral edge 121 and the medial edge 123 may be curved. For example, as shown in FIG. 2A, the one or more structural support inserts 108 may include a curved lateral edge 121 and a curved medial edge 123. In embodiments, the curved lateral edge 121 of the structural support inserts 108 may be defined by an arc defining a portion of a circle. For example, the curved lateral edge 121 may be defined by a 180° arc defining a semicircle. By way of another example, the curved lateral edge 121 may be defined by an arc defining a sector of a circle, wherein the angle defining the arc is less than 180° such that the sector of the circle defined by the arc is smaller than a semicircle, as shown in FIG. 2A. The curved medial edge 123 may include a convex curve with respect to a central plane 101 of the adjustable orthotic foot device 100.

It is contemplated herein that features and characteristics of the structural support insert 108 shown and described may facilitate improved fit and functionality of the one or more structural support inserts 108 within the pocket 114. For example, it is contemplated herein that a curved medial edge 123 of the structural support inserts 108 may facilitate the ability of the one or more structural support inserts 108 to be disposed within the pocket 114 such that the medial edge 123 of the one or more structural support inserts 108 is flush (or substantially flush) with the medial edge of the soft insole layer 104 and/or shell layer 102, as noted previously herein. Similarly, it is contemplated herein that a curved lateral edge 121 defined by an arc which is less than 180° may allow for the structural support insert 108 to substantially conform to the cross-sectional shape of the pocket 114, while simultaneously ensuring the medial edge 123 of the one or more structural support inserts 108 is flush (or substantially flush) with the medial edge of the soft insole layer 104 and/or shell layer 102.

As shown in FIG. 2A, the one or more structural support inserts may exhibit varying sizes. For example, as shown in FIG. 2A, a first structural support insert 108a may include a first cross-sectional area, and a second structural support insert 108b may include a second cross-sectional area which is smaller than the first cross-sectional area. It is noted that structural support inserts 108 of varying sizes may allow for multiple structural support inserts 108 to be disposed within the pocket 114 simultaneously such that a slope/profile of the arch support structure 110 conforms naturally with an increase in the arch support structure 110 height as the structural support inserts 108 are added to the pocket on top of one another. In particular, it is noted herein that structural support inserts 108 of varying heights may allow for multiple structural support inserts 108 to substantially fill and conform to the shape of the pocket 114 as additional structural support inserts are added.

In additional and/or alternative embodiments, the one or more structural support inserts 108 may be smaller than the pocket 114 itself such that the one or more structural support inserts 108 may be moved around within the pocket 114. As noted previously herein, individuals have unique foot structures that vary from person to person. In this regard, the apex of an arch of one person's foot may be at a different position than the apex of an arch of another person's foot. Accordingly, it is contemplated herein that the ability to move the one or more structural support inserts 108 within the pocket 114 may enable improved flexibility to modify the shape of the adjustable orthotic foot device 100 in order to provide improved support and comfort to a wide variety of foot shapes and sizes.

For example, referring to FIG. 1C, the one or more structural support inserts 108 may be smaller than the pocket 114 such that they may be moved around within the pocket 114. In this example, the one or more structural support inserts 108 may be slid forward within the pocket such that the arch support structure 110 is disposed closer to the toe of the adjustable orthotic foot device 100. By way of another example, the one or more structural support inserts 108 may be slid backward within the pocket such that the arch support structure 110 is disposed closer to the heel of the adjustable orthotic foot device 100. It is contemplated that the one or more structural support inserts 108 may be moved in any direction within the pocket in order to adjust both the height and position of the arch support structure 110.

Figure 2B:
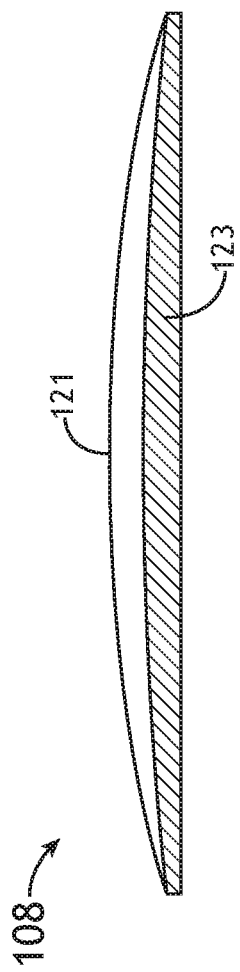
FIG. 2B is a side elevation view of a structural support insert, in accordance with one or more embodiments of the present disclosure.

FIG. 2B is a side elevation view of a structural support insert 108, in accordance with one or more embodiments of the present disclosure.

In embodiments, the one or more structural support inserts 108 include a maximum thickness at a midpoint of the curved medial edge 123 of the one or more structural support inserts 108. For example, as shown in FIG. 2B, the structural support insert 108 may exhibit the maximum thickness at the midpoint of the curved medial edge 123, such that the thickness of the structural support insert 108 tapers off as you move along the curved medial edge 123 from the midpoint to the distal ends of the structural support insert 108. In this regard, in some embodiments, the thickness of the one or more structural support inserts 108 may decrease moving along the one or more structural support inserts 108 in a radial direction from the midpoint of the curved medial edge 123 to the curved lateral edge 121 of the one or more structural support inserts 108. For example, referring to FIG. 2A, the thickness of the structural support inserts 108 may be greatest at the midpoint of the curved medial edge 123 and taper off in a radial direction, such that thickness contour lines surround the midpoint of the curved medial edge 123 in a radial direction. It is contemplated herein that structural support inserts 108 with thickness profiles shown and described may allow the structural support inserts 108 to substantially conform to the shape of the pocket 114 and provide a natural arch support structure 110 which may effectively provide comfort and support to a user.

Figure 3A:
FIG. 3A is a perspective view of an adjustable orthotic foot device, in accordance with one or more embodiments of the present disclosure.
Figure 3B:
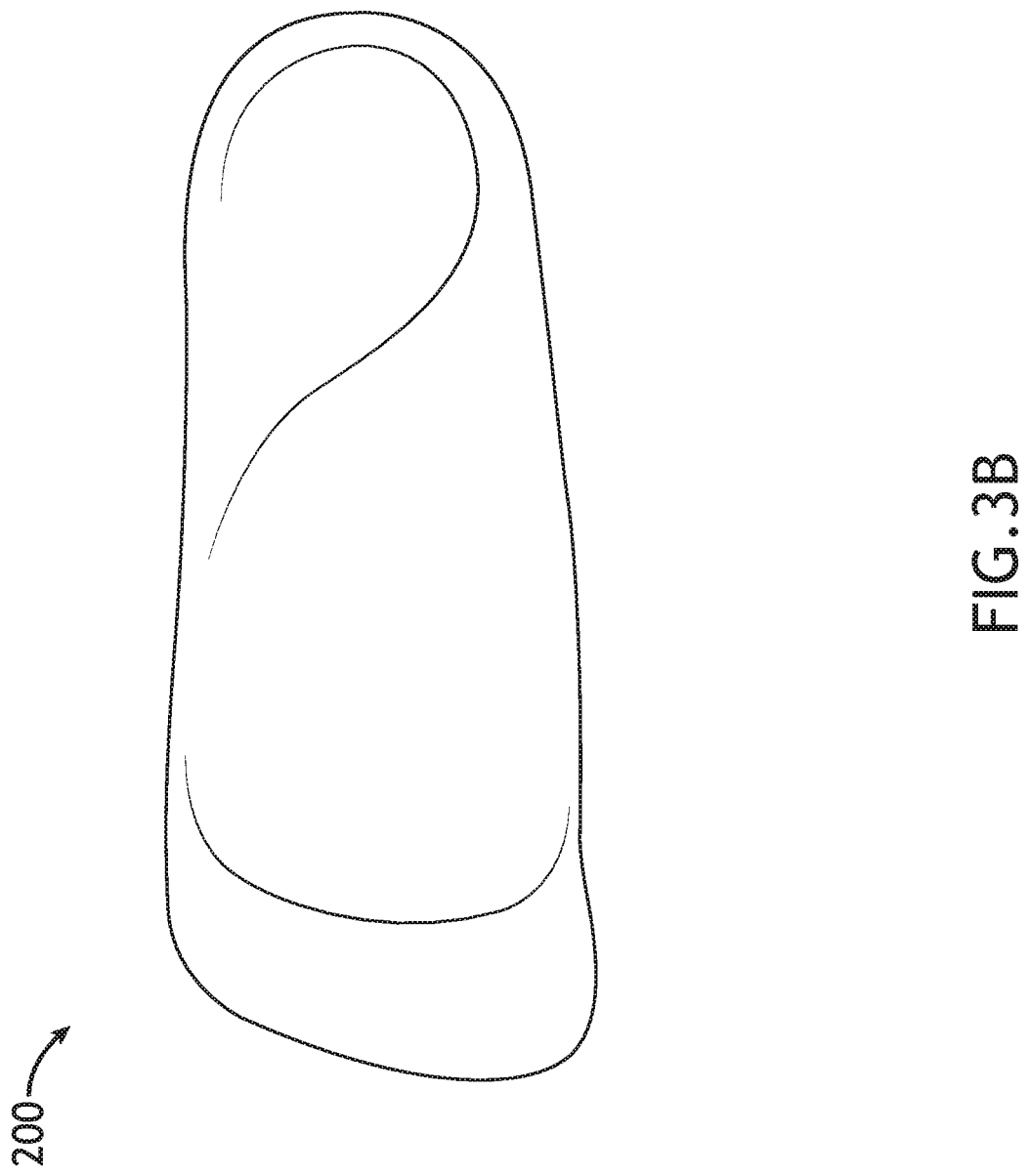
FIG. 3B is a top view of an adjustable orthotic foot device, in accordance with one or more embodiments of the present disclosure.
Figure 3C:
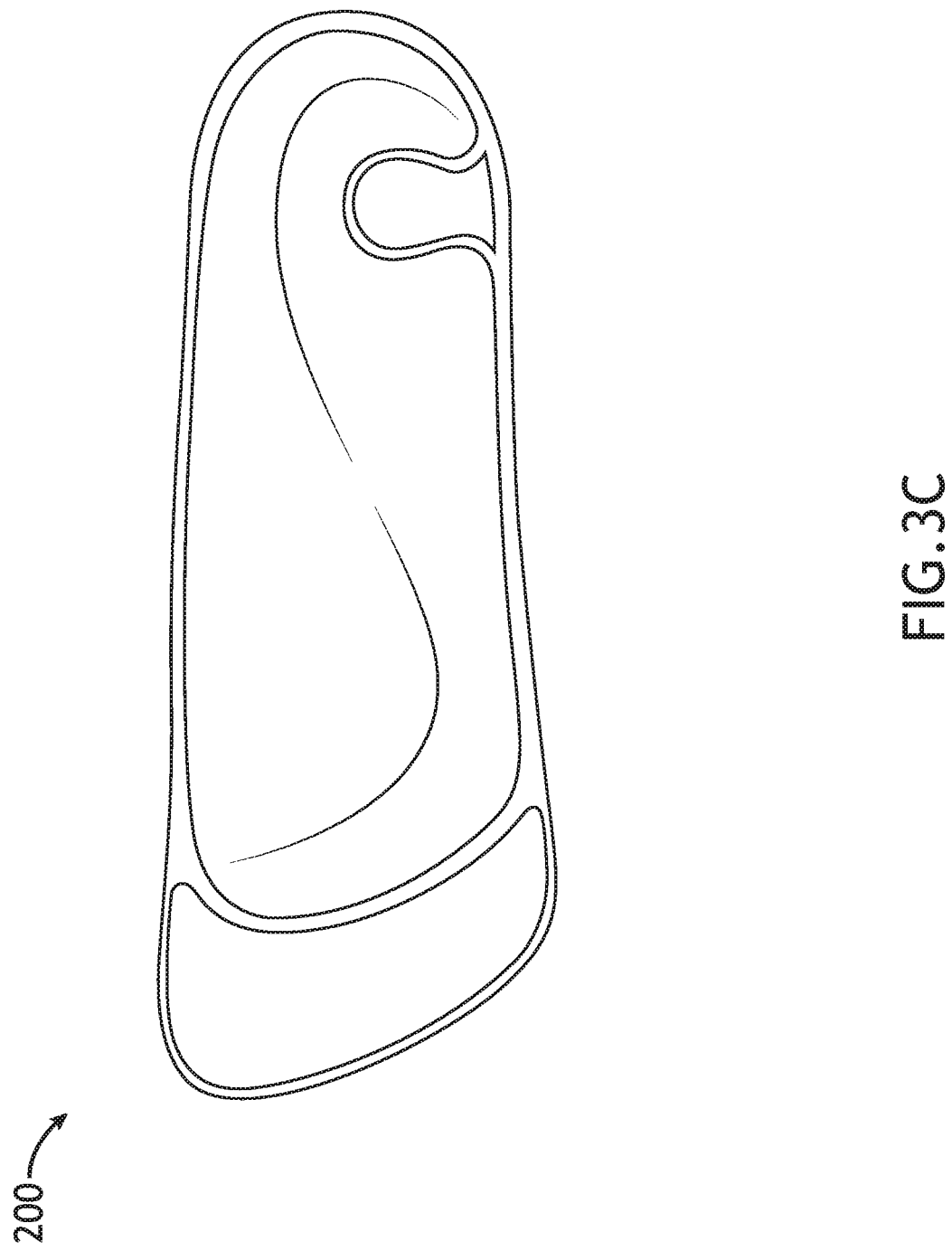
FIG. 3C is a bottom view of an adjustable orthotic foot device, in accordance with one or more embodiments of the present disclosure.
Figure 3D:
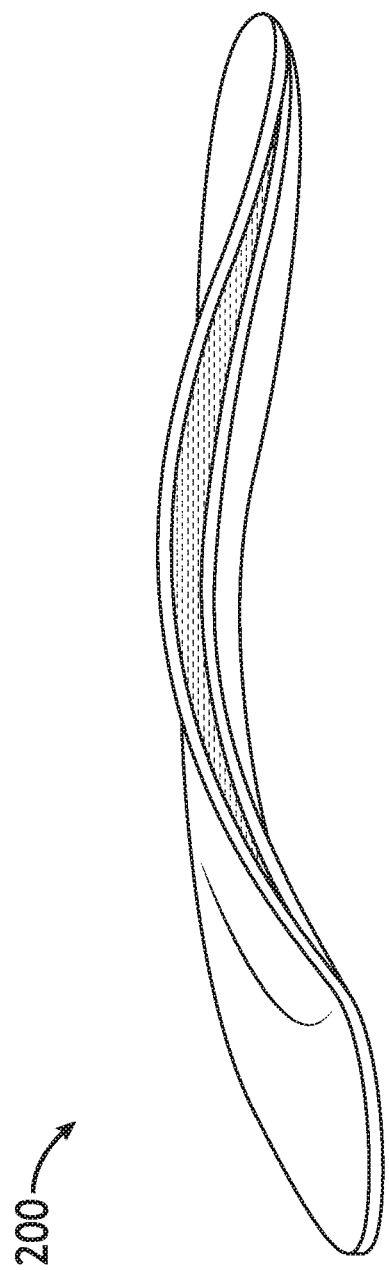
FIG. 3D is a side elevation view of an adjustable orthotic foot device, in accordance with one or more embodiments of the present disclosure.
Figure 3E:
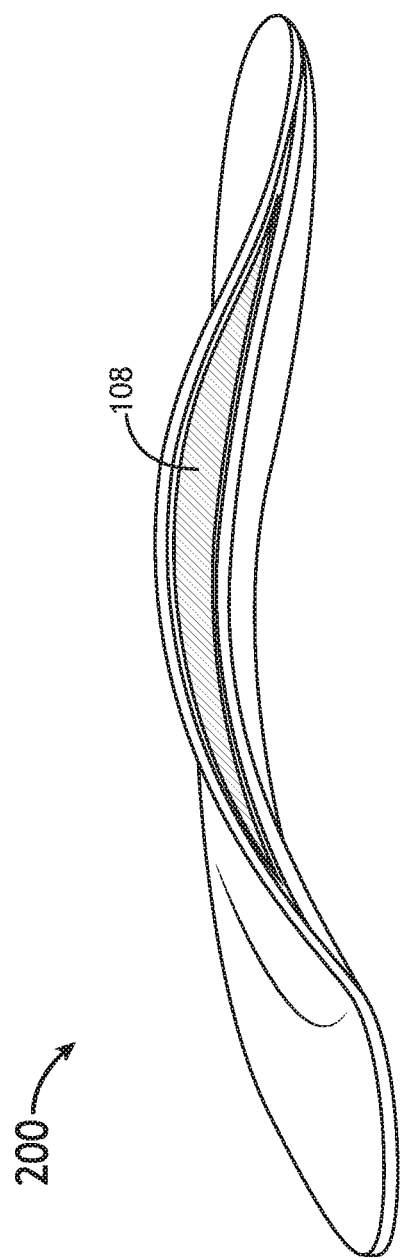
FIG. 3E is a side view of an adjustable orthotic foot device including one structural support insert, in accordance with one or more embodiments of the present disclosure.

FIG. 3A is a perspective view of an adjustable orthotic foot device 200, in accordance with one or more embodiments of the present disclosure. FIG. 3B is a top view of an adjustable orthotic foot device 200, in accordance with one or more embodiments of the present disclosure. FIG. 3C is a bottom view of an adjustable orthotic foot device 200, in accordance with one or more embodiments of the present disclosure. FIG. 3D is a side elevation view of an adjustable orthotic foot device 200, in accordance with one or more embodiments of the present disclosure. FIG. 3E is a side view of an adjustable orthotic foot device 200 including one structural support insert 108, in accordance with one or more embodiments of the present disclosure.

As noted previously herein, the adjustable orthotic foot device 100 of the present disclosure may be implemented in the context of any footwear article known in the art including, but not limited to, tennis shoes, running shoes, dress shoes, boots, sandals, heeled shoes, and the like. For example, FIGS. 3A-3E illustrates an adjustable orthotic foot device 200 configured to be worn in a heeled shoe. In this regard, the adjustable orthotic foot device 200 may be shaped in such a manner as to conform to a heeled shoe. It is noted herein that any description associated with the adjustable orthotic foot device 100 depicted in FIGS. 1A-1J may be regarded as applying to the adjustable orthotic foot device 200 shown in FIGS. 3A-3E, unless noted otherwise herein.

FIG. 4 is a flowchart of a method 400 for producing an adjustable orthotic foot device, in accordance with one or more embodiments of the present disclosure. It is noted herein that the steps of method 400 may be implemented all or in part by adjustable orthotic foot device 100. It is further recognized, however, that the method 400 is not limited to the adjustable orthotic foot device 100 in that additional or alternative system-level embodiments may carry out all or part of the steps of method 400.

In a step 402, a shell layer is formed. For example, as shown in FIG. 1C, the shell layer 102 may be configured to be disposed within a footwear article. In this regard, the shell layer 102 may include an upper surface and a contoured lower surface, wherein the contoured lower surface of the shell layer 102 is contoured such that it conforms to at least a portion of a profile of a footwear article when disposed within the footwear article.

In a step 404, a soft insole layer is formed. For example, as shown in FIG. 1A and FIG. 1D, the soft insole layer 104 may include an upper surface defining an arch support structure 110 along a medial edge of the soft insole layer 104.

In a step 406, a plastic layer is coupled to at least a portion of a lower surface of the soft insole layer. For example, as shown in FIG. 1B, a removable plastic layer 116 may be coupled to at least a portion of the lower surface of the soft insole layer 104 which is directly beneath the arch support structure 110 of the soft insole layer 104.

In a step 408, the plastic layer and/or at least a portion of the soft insole layer is coupled to the upper surface of the shell layer. For example, as shown in FIG. 1A, the removable plastic layer 116 and the portion of the lower surface of the soft insole layer 104 not covered by the plastic layer 116 may be coupled to the upper surface of the shell layer 102.

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed is:
1. An adjustable orthotic foot device, comprising:
a shell layer including an upper surface and a contoured lower surface, wherein the contoured lower surface of the shell layer is contoured such that it conforms to at least a portion of a profile of an inner surface of a footwear article when disposed within the footwear article;
a soft insole layer coupled to the upper surface of the shell layer, the soft insole layer defining an arch support structure on an upper surface of the soft insole layer along a medial edge of the soft insole layer, wherein the soft insole layer is formed with one or more elastically compressible materials;
one or more structural support inserts configured to be removably inserted within a pocket formed between the shell layer and the soft insole layer directly beneath the arch support structure in order to adjust an arch height of the arch support structure; and a removable plastic layer disposed between a portion of the upper surface of the shell layer and a portion of a lower surface of the soft insole layer, the removable plastic layer is coupled to upper surface of the shell layer and the lower surface of the soft insole layer with one or more adhesives, wherein the one or more structural support inserts are defined by a curved lateral edge and a curved medial edge, wherein the curved medial edge comprises a convex curve with respect to a central plane of the adjustable orthotic foot device, wherein the one or more structural support inserts are configured to be removably inserted within the pocket such that the medial edge of the one or more structural support inserts are substantially flush with the medial edge of the soft insole layer, and wherein the soft insole layer is coupled to the top surface of the shell layer via a first set of one or more adhesives and a second set of one or more adhesives, wherein the first set of one or more adhesives are configured to permanently couple the soft insole layer to a first portion of the top surface of the shell layer, wherein the second set of one or more adhesives are configured to impermanently couple the soft insole layer to a second portion of the top surface of the shell layer different from the first portion when the removable plastic layer is removed, the second set of adhesives being configured to allow a user to separate the soft insole layer to the second portion of the top surface of the shell layer for insertion of one or more structural inserts, wherein the second portion of the top surface of the shell layer defines a cross section of the pocket formed between the shell layer and the soft insole layer.

2. The adjustable orthotic foot device of claim 1, wherein a cross sectional area of the removable plastic layer defines a cross sectional area of the pocket.

3. The adjustable orthotic foot device of claim 1, wherein removal of the removable plastic layer from between the shell layer and the soft insole layer forms the pocket between the shell layer and the soft insole layer.

4. The adjustable orthotic foot device of claim 1, wherein the removable plastic layer further includes a pull-tab portion which extends beyond the medial edge of the soft insole layer, wherein the pull-tab portion is configured to facilitate removal of the plastic tab layer.

5. The adjustable orthotic foot device of claim 1, the pocket is defined by a portion of a lower surface of the soft insole layer and a portion of the upper surface of the shell layer, wherein the portion of the lower surface of the soft insole layer and the portion of the upper surface of the shell layer include one or more adhesives configured to secure the one or more structural support inserts within the pocket.

6. The adjustable orthotic foot device of claim 1, wherein at least one of an upper surface or a lower surface of the one or more structural support inserts include an adhesive layer configured to secure the one or more structural support inserts within the pocket.

7. The adjustable orthotic foot device of claim 6, wherein the one or more structural support inserts further include a removable cover disposed on the adhesive layer.

8. The adjustable orthotic foot device of claim 1, wherein the curved lateral edge of the one or more structural support inserts is defined by an arc defining a sector of a circle, wherein an angle defining the arc is less than 180°.

9. The adjustable orthotic foot device of claim 1, wherein the one or more structural support inserts comprise:

a first structural support insert including a first cross-sectional area; and one or more additional structural support inserts including one or more additional cross-sectional areas smaller than the first cross-sectional area.

10. The adjustable orthotic foot device of claim 9, wherein the first structural support insert is configured to be removably inserted within the pocket such that it is disposed on the upper surface of the shell layer, wherein the one or more additional structural support inserts are configured to be removably inserted within the pocket between an upper surface of the first structural support insert and a lower surface of the soft insole layer.

11. The adjustable orthotic foot device of claim 1, wherein the medial edge of the soft insole layer comprises a convex medial edge with respect to the central plane of the adjustable orthotic foot device.

12. The adjustable orthotic foot device of claim 1, wherein the one or more structural support inserts include a maximum thickness at a midpoint of the medial edge of the one or more structural support inserts.

13. The adjustable orthotic foot device of claim 12, wherein a thickness of the one or more structural support inserts decreases moving along the one or more structural support inserts in a radial direction from the midpoint of the curved medial edge to the curved lateral edge of the one or more structural support inserts.

14. The adjustable orthotic foot device of claim 1, wherein a void defined by the pocket between the shell layer and the soft insole layer is configured to be closed upon removal of the one or more structural support inserts from the pocket such that a lower surface of the soft insole layer is disposed on the upper surface of the shell layer upon removal of the one or more structural support inserts from the pocket.

15. The adjustable orthotic foot device of claim 1, further comprising one or more additional pockets formed between the shell layer and the soft insole layer, the one or more additional pockets configured to receive one or more additional structural support inserts in order to adjust a profile of the upper surface of the soft insole layer.

16. The adjustable orthotic foot device of claim 1, wherein the shell layer is formed from at least one of plastic or ethylene vinyl acetate.

17. The adjustable orthotic foot device of claim 1, wherein the soft insole layer includes at least one of an anti-bacterial material, a fungicidal material, or an anti-odorous material.

18. The adjustable orthotic foot device of claim 17, wherein the anti-odorous material comprises at least one of a bamboo material or a charcoal fiber material.

* * * * *